US012651670B2

(12) United States Patent
Narayanan

(10) Patent No.: US 12,651,670 B2
(45) Date of Patent: Jun. 9, 2026

(54) APPARATUS AND METHOD FOR MONITORING VITAL SIGNS AND PREDICTING CRITICAL ILLNESS

(71) Applicant: Nishant Narayanan, Palatine, IL (US)

(72) Inventor: Nishant Narayanan, Palatine, IL (US)

( * ) Notice: Subject to any disclaimer, the term of this patent is extended or adjusted under 35 U.S.C. 154(b) by 0 days.

(21) Appl. No.: 19/171,204

(22) Filed: Apr. 5, 2025

(65) Prior Publication Data

US 2025/0232882 A1    Jul. 17, 2025

Related U.S. Application Data

(63) Continuation-in-part of application No. 18/582,439, filed on Feb. 20, 2024.

(51) Int. Cl.
*G16H 50/30* (2018.01)
*G16H 10/60* (2018.01)
*G16H 40/67* (2018.01)

(52) U.S. Cl.
CPC ............. *G16H 50/30* (2018.01); *G16H 10/60* (2018.01); *G16H 40/67* (2018.01)

(58) Field of Classification Search
None
See application file for complete search history.

(56) References Cited

U.S. PATENT DOCUMENTS

2016/0240100 A1 * 8/2016 Rauhala ............. G09B 19/0038
2020/0281480 A1 * 9/2020 Tran ..................... A61B 5/6813

FOREIGN PATENT DOCUMENTS

WO    WO-2025147613 A1 * 7/2025

OTHER PUBLICATIONS

Rahman et al., Mental Stress Recognition using K-Nearest Neighbor (KNN) Classifier on EEG Signals, Int'l Conf. Materials, Electronics & Information Engineering (ICMEIE) (Jun. 2015) (Year: 2015).*

* cited by examiner

*Primary Examiner* — Jonathon A. Szumny
*Assistant Examiner* — Nicholas Akogyeram, II
(74) *Attorney, Agent, or Firm* — NOVEL PATENT SERVICES LLC

(57)    ABSTRACT

Apparatus and methods are disclosed for monitoring, tracking, and storing vital signs using an adjustable wristband and/or ring designed to fit the patient or user. The apparatus includes integrated components such as sensors, a motherboard, and a web-based platform and/or mobile dashboard. The apparatus work together to notify the patient, healthcare team, and family members when vital signs are abnormal. Additionally, the system displays and securely stores vital signs data, making it accessible to authorized individuals during medical care or for daily health monitoring. The apparatus provides real-time notifications to users upon detecting abnormal vital signs and utilizes artificial intelligence (AI) and machine learning models to analyze health data collected from multiple data sources including EMR systems, multiple personal devices and payers to predict risk to critical illness, recommend preventive care options, and deliver proactive, personalized health insights to users, enhancing remote patient management, improving patient outcomes and overall efficiency.

16 Claims, 15 Drawing Sheets

100

150

140

130

110

120

100

140

150

130

120

110

500

600

700

1100

140

120

APPARATUS AND METHOD FOR MONITORING VITAL SIGNS AND PREDICTING CRITICAL ILLNESS

TECHNICAL FIELD

The present disclosure relates to body vital sign monitoring systems and, more specifically, to an apparatus and method for continuously monitoring vital signs, securely storing the collected data, and providing real-time notifications to users upon detecting abnormal vital signs. Additionally, the invention utilizes artificial intelligence (AI) and machine learning models to analyze health data collected from multiple data sources like Electronic Medical Records (EMR) systems, other personal devices, payers to accurately predict risk to critical illness and recommend preventive care options. The invention also provides a conversational type personal assistant to help patients manage their health risks and deliver proactive, personalized health insights to users, thereby enhancing remote patient management, quality of care, improving patient outcomes and overall healthcare efficiency.

BACKGROUND

Accurate and consistent measurement of vital signs is essential for effective patient care, as it enables timely medical intervention and improves health outcomes. Vital signs, such as body temperature, heart rate, blood pressure, glucose levels, respiratory rate, and blood oxygen levels, provide critical insights into a patient's overall health status. Continuous monitoring of these parameters is particularly important for individuals with chronic conditions, elderly patients, post-operative recovery cases, and individuals at risk of sudden health deterioration.

Although various monitoring devices are available for tracking individual vital signs, such as thermometers for body temperature, pulse oximeters for oxygen saturation, and blood pressure monitors, these devices often function independently and require manual readings or periodic assessments. Additionally, current monitoring approaches are not targeted towards the amalgamation of the patient, care team, and family members nor do they alert the care team and family members if one of the vitals are out of range. This fragmented approach can lead to gaps in data collection, delays in identifying critical health issues, and a lack of real-time insights for caregivers and medical professionals. Patients visits multiple providers and collect information in multiple personal devices to manage their health. Currently there is no device that combines data from multiple devices, provider systems and payer sources to make a reliable and accurate prediction. Lack of access to holistic view of patient's data to the medical practitioners and patients themselves leads to inaccurate diagnosis and bad patient outcomes thereby increasing healthcare costs.

There is an increasing need for an integrated, holistic health monitoring system that can continuously track a comprehensive range of vital signs, store the collected data, combines data from multiple sources and share it remotely with authorized individuals, including healthcare providers, caregivers, and family members. Such a system would enable proactive health management, allowing for early detection of abnormalities and immediate medical response. Additionally, automated alerts and notifications when vital signs exceed safe thresholds could help prevent medical emergencies by ensuring timely intervention.

In light of these challenges, a system that seamlessly monitor vital signs, glucose levels, and blood pressure of a user in real-time while securely storing and managing user-related data to ensure privacy and reliability. There is also a need for a system that send notifications to the users in response to abnormal readings or potential health risks, enabling timely intervention. Further, there is also a need for a system that continuously analyzes data collected from wearable devices, third party personal or fitness devices used by patients, electronic medical records systems, and payer data to predict risk to critical illness, and recommends preventive care options, and provide proactive, personalized health insights to users by leveraging artificial intelligence (AI) and machine learning models.

SUMMARY

In one aspect, the invention provides an apparatus that syncs with a web-based or mobile platform to display and store a user's vital signs, including heart rate, body temperature, oxygen level, mental state resilience, and hydration levels. In some embodiments, the apparatus includes a sensor attached to a ring that is configured to measure various vital signs, a motherboard attached to a wristband, and a cable connecting the sensor to the motherboard.

In some embodiments, the apparatus connects to a mobile dashboard or web platform. The mobile dashboard or web platform contains an input screen for the user to input unique, customizable minimum and maximum thresholds for their vital signs. The mobile dashboard or web platform also contains input screens to set up notifications and grant access to authorized third parties, such as the user's health care team and family. The mobile dashboard or web platform also contains an input screen to customize the unique notification, alert, or warning message related to the vital sign. The mobile dashboard or web platform will automatically send the unique notification, alert, or warning when the user's vital sign is outside the designated range.

In certain aspects, the present disclosure provides a device and non-transitory computer readable medium storing program instructions that are executable to monitor, track, and store vital signs, comprising: an input screen on a mobile dashboard or web platform to enter a minimum value and a maximum values for vital signs; a vitals sensor that reads vital sign data at regular intervals; a ring in which the vitals sensor is placed; a connective cable that sends the vital sign data from the sensor, a motherboard that receives the vital sign data from the sensor through the connective cable; and a wristband in which the motherboard is placed; wherein the motherboard contains a coding algorithm that calculates and compares the vital sign data to the inputted minimum value and the inputted maximum values for vital signs; wherein the motherboard sends the vital sign data to the mobile dashboard or web platform through a communication network, wherein the mobile dashboard or web platform processes and displays the vital sign data; and wherein the mobile dashboard or web platform displays an alert when the vital sign data is outside of the inputted minimum value and the inputted maximum values for the vital signs. In certain embodiments, the device and non-transitory computer readable medium stores additional program instructions that are executable to display historical trends of vitals data in a chart, graph, or timeline. In certain embodiments, the device and non-transitory computer readable medium stores additional program instructions that are executable to determine when vital signs have been increasing or decreasing over time; wherein the consistent variability in vital sign over time indicates the severity of the associated health complication; and send an alert or notification immediately, in two minutes, or in thirty minutes depending on the severity of the associated health complication.

In certain aspects, the present disclosure provides a method of monitoring, tracking. and storing vitals data, comprising: reading vitals data with a vitals sensor at regular intervals; sending vitals data from the vitals sensor to a motherboard through a connective cable; calculating and comparing vitals data through a coding algorithm within the motherboard; sending the vitals data to a mobile dashboard or web platform through a communication network; and displaying the vitals data on the mobile dashboard or web platform. In certain embodiments, the method comprises inputting a minimum value and a maximum value associated with the vital sign; and sending an alert or notification when the vitals data is out of the range determined by the input minimum value and the input maximum value.

In certain aspects, the present disclosure provides an apparatus to monitor, track, and store vital signs. The apparatus comprises a sensing device, a wearable device, a wristband, a data processing unit, an artificial intelligence module, and a machine learning model.

In one embodiment, the sensing device to monitor data related to physiological health parameters of a user at regular intervals. The data related to the physiological health parameters comprises, but is not limited to, glucose levels and blood pressure.

In one embodiment, the wearable device is configured to be worn on at least one finger of a user's hand. The wearable device is configured to support the sensing device. The wristband is configured to allow the user to wear on a wrist. The wristband comprises a processor and a non-transitory computer readable medium for storing program instructions that are executable by the processor.

In one embodiment, the data processing unit is configured to receive the data related to the physiological health parameters of the user from the sensing device. The data processing unit is further configured to collect medical records and health plan data of the user from a third party personal, fitness devices used by the user, electronic medical records systems and diagnostic codes of the user from providers and payers. The server is further configured to analyze the data related to the physiological health parameters, the medical records, and the health plan data through the data processing unit. In a preferred embodiment, the data related to the physiological health parameters, the medical records, and the health plan data are compared with predefined health risk threshold values by the server through an artificial intelligence module.

In one embodiment, the server is further configured to predict risk to critical illness and provide preventive care options, proactive and personalized insights to the user through a computing device. The processor further provides a personal assistant to the user to monitor progress on preventive care options and manage wellbeing of the user through the computing device.

In one embodiment, the server is further configured to determine if the user needs to take precautions to manage health and prevent critical illness through a machine learning model. The data related to the physiological health parameters and the precautions are displayed to the user through the computing device. In one embodiment, the machine learning model is a k-nearest neighbors (KNN) model, which is configured to classify user health states and determine the preventive care options. The preventive care options comprise, but are not limited to, dietary changes, exercise regimens, and medication reminders.

In one embodiment, the server is configured to send one or more alerts to the user in response to detection of abnormal vital signs. The server is further configured to generate at least one progress report based on the physiological health parameters for the user and share through the computing device. The server is further configured to generate charts and graphs with timelines to visualize physiological health parameters and display them through the computing device. In one embodiment, the apparatus is configured to wirelessly communicate with a server, the fitness devices and computing devices through a network.

In one embodiment, a method for monitoring, tracking, and storing vitals data through the apparatus is disclosed in accordance with another exemplary embodiment of the invention. At one step, the sensing device monitors the physiological health parameters of a user at regular intervals. The sensing device is supported by the wearable device. At another step, the processor disposed within the wristband transfers received data related to the physiological health parameters of the user to the server via the network. At another step, the server collects and analyzes the data related to the physiological health parameters, the medical records and the health plan data of the user from a third party personal, fitness devices used by the user, electronic medical records systems and diagnostic codes of the user from providers and payers through the data processing unit for comparing with predefined health risk threshold values through the artificial intelligence module. At another step, the server predicts risk to critical illness and provide preventive care options, proactive and personalized insights to the user through the computing device, and provide a personal assistant to the user to monitor progress on preventive care options and manage wellbeing of the user. Further, at another step, the server determines if the user needs to take precautions to manage health and prevent critical illness through the machine learning model, and displaying the data related to the physiological health parameters and the precautions to the user through the computing device.

BRIEF DESCRIPTION OF THE DRAWINGS

The following figures depict illustrative embodiments of the invention.

5

6

Figure 8:
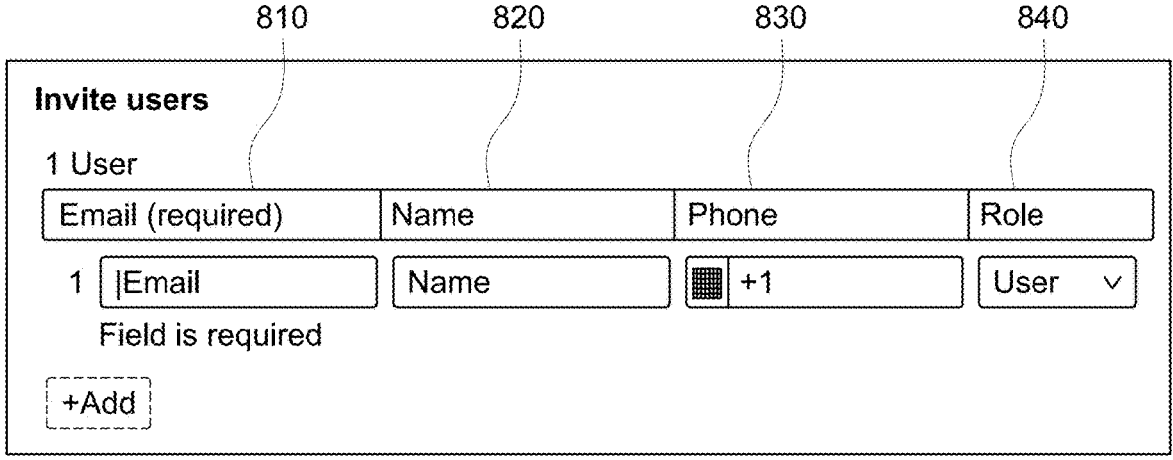

FIG. 8 is an exemplary illustration of the mobile dashboard screen for the user or other qualified representative to grant access to others to view the user's vitals information and stored data.

Figure 9:
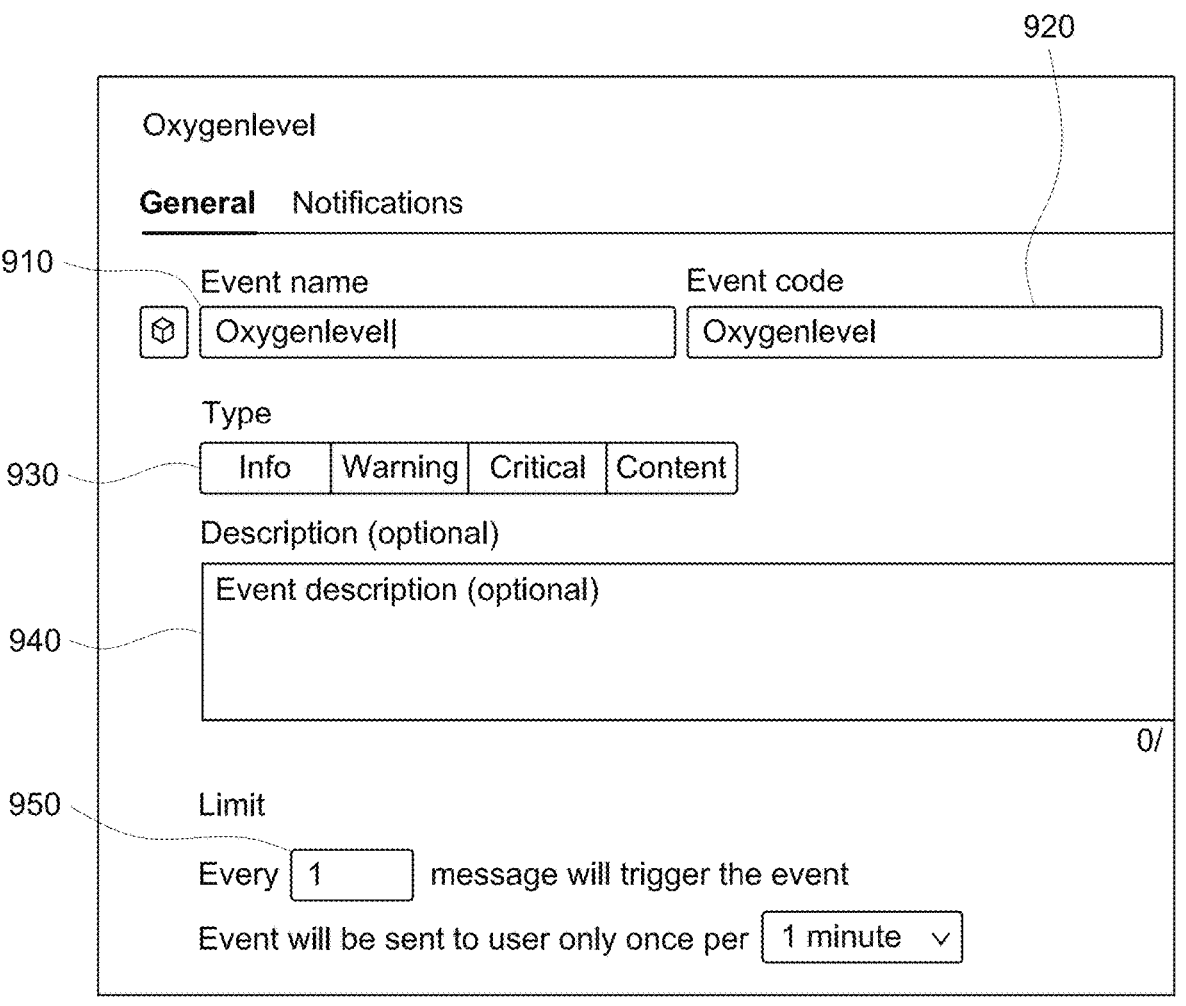

FIG. 9 is an exemplary illustration of the mobile dashboard screen to customize warning, alert, or notification messages when vitals are outside of the user's designated minimum and maximum vitals range.

Figure 10:
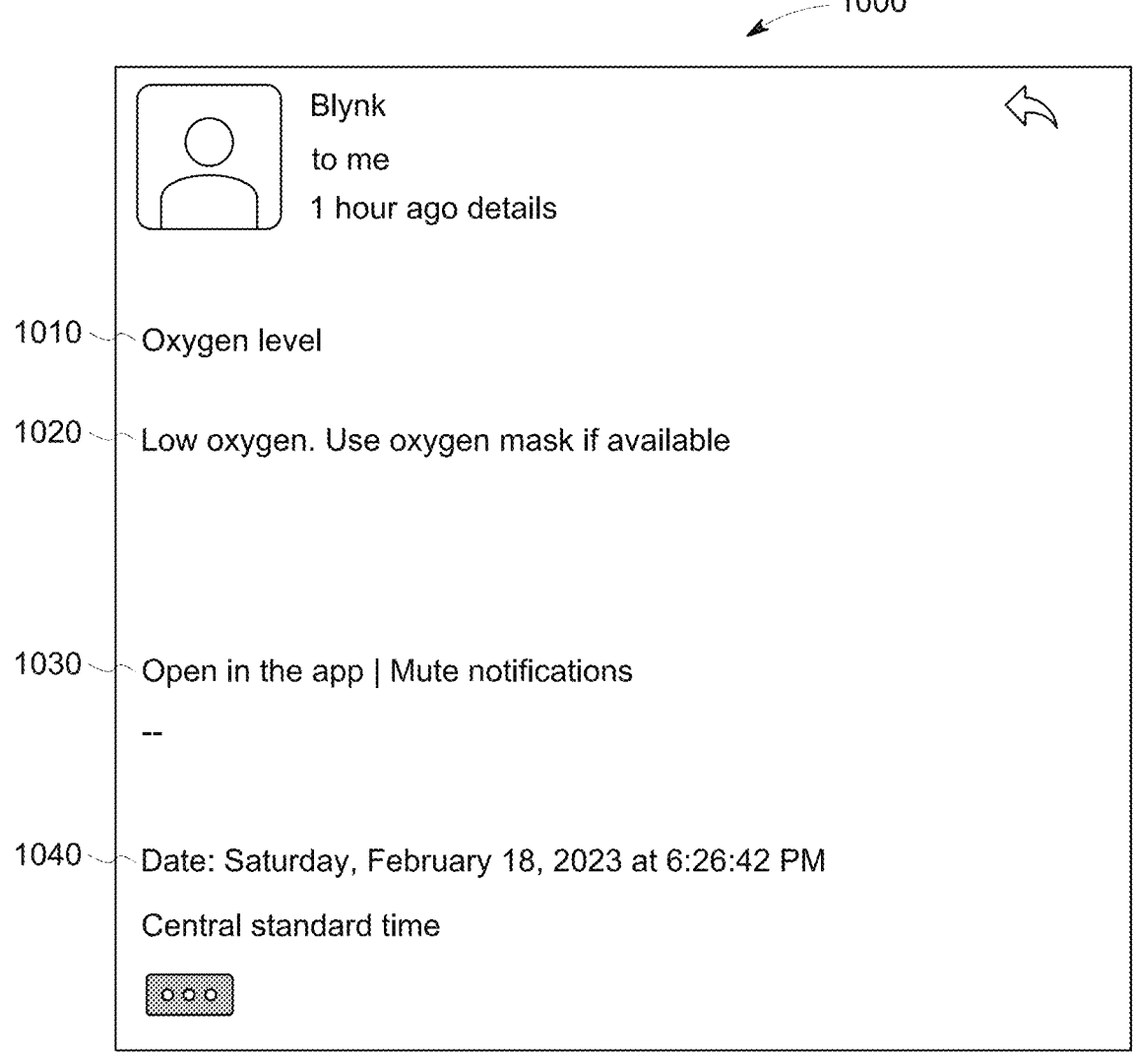

FIG. 10 is an exemplary illustration of an email alert when the user's vital sign is out of the user's designated range.

Figure 11A:
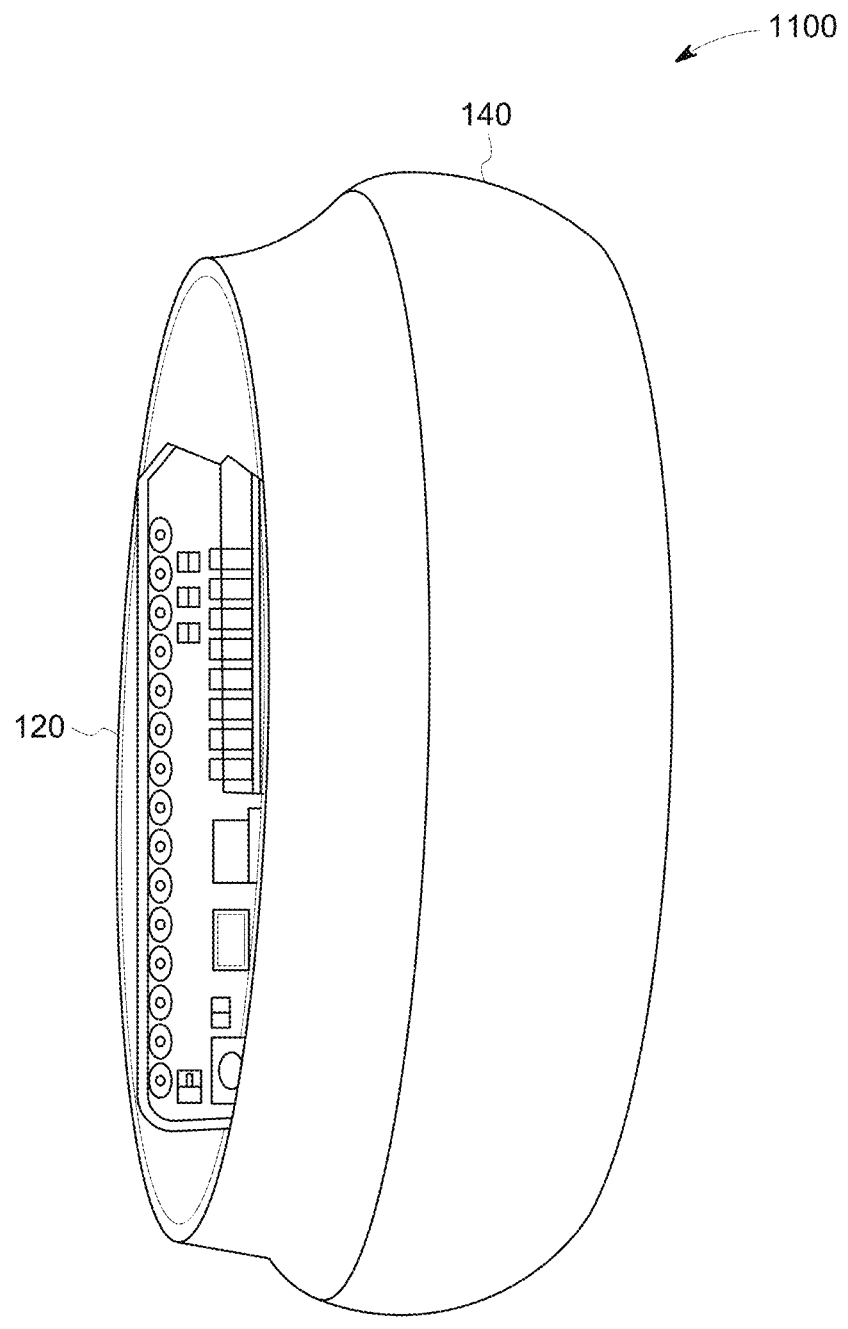
Figure 11B:
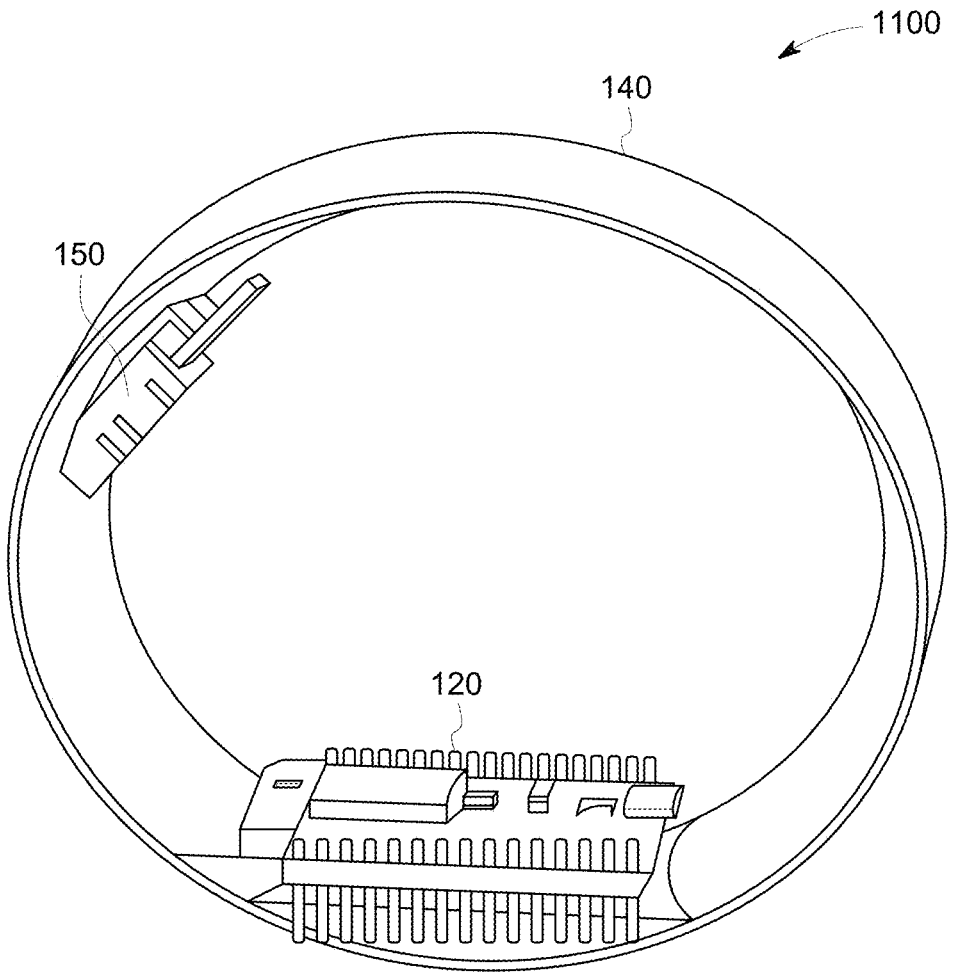

FIGS. 11A-11B are exemplary illustrations of a ring extension configuration of the apparatus.

Figure 12A:
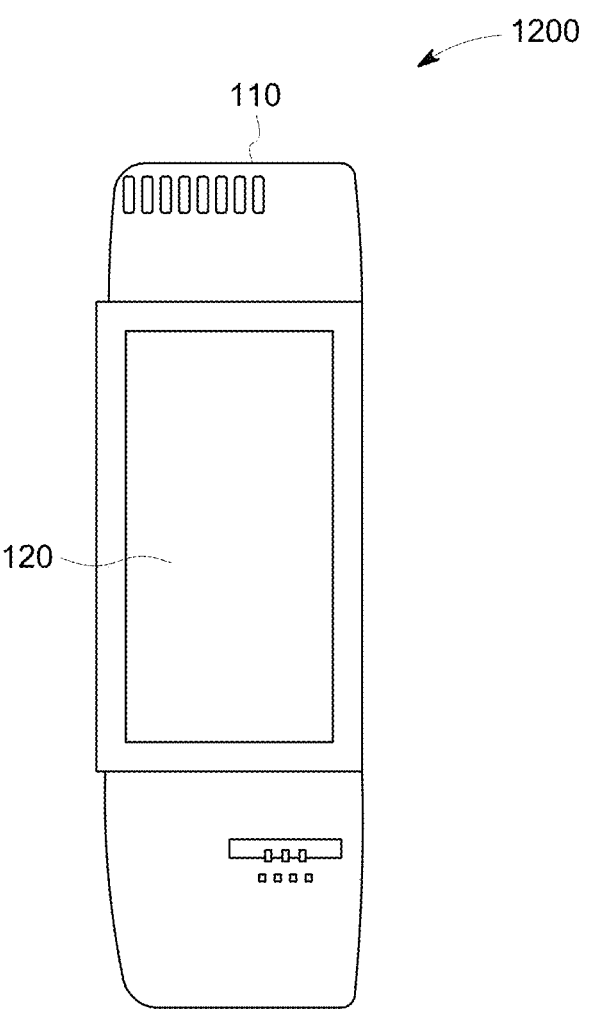
Figure 12B:
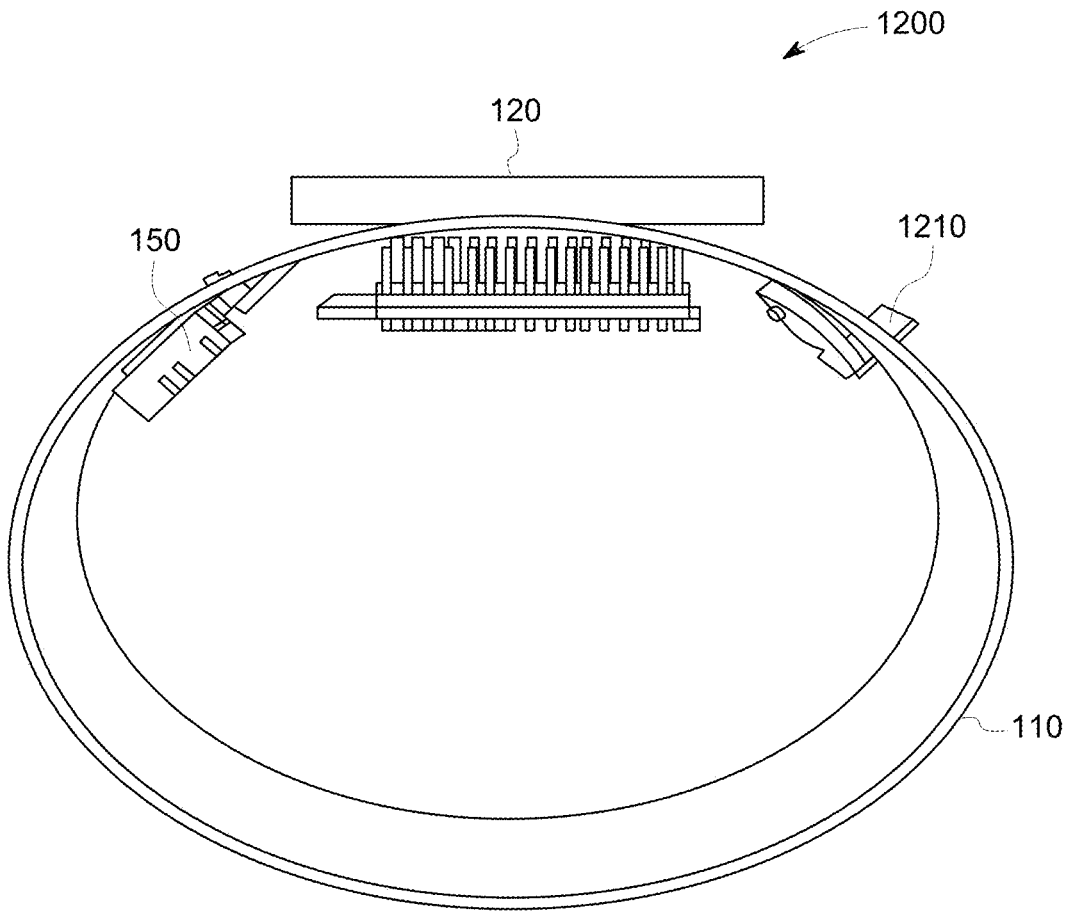

FIGS. 12A-12B are exemplary illustrations of a bracelet configuration of the apparatus.

Figure 13:
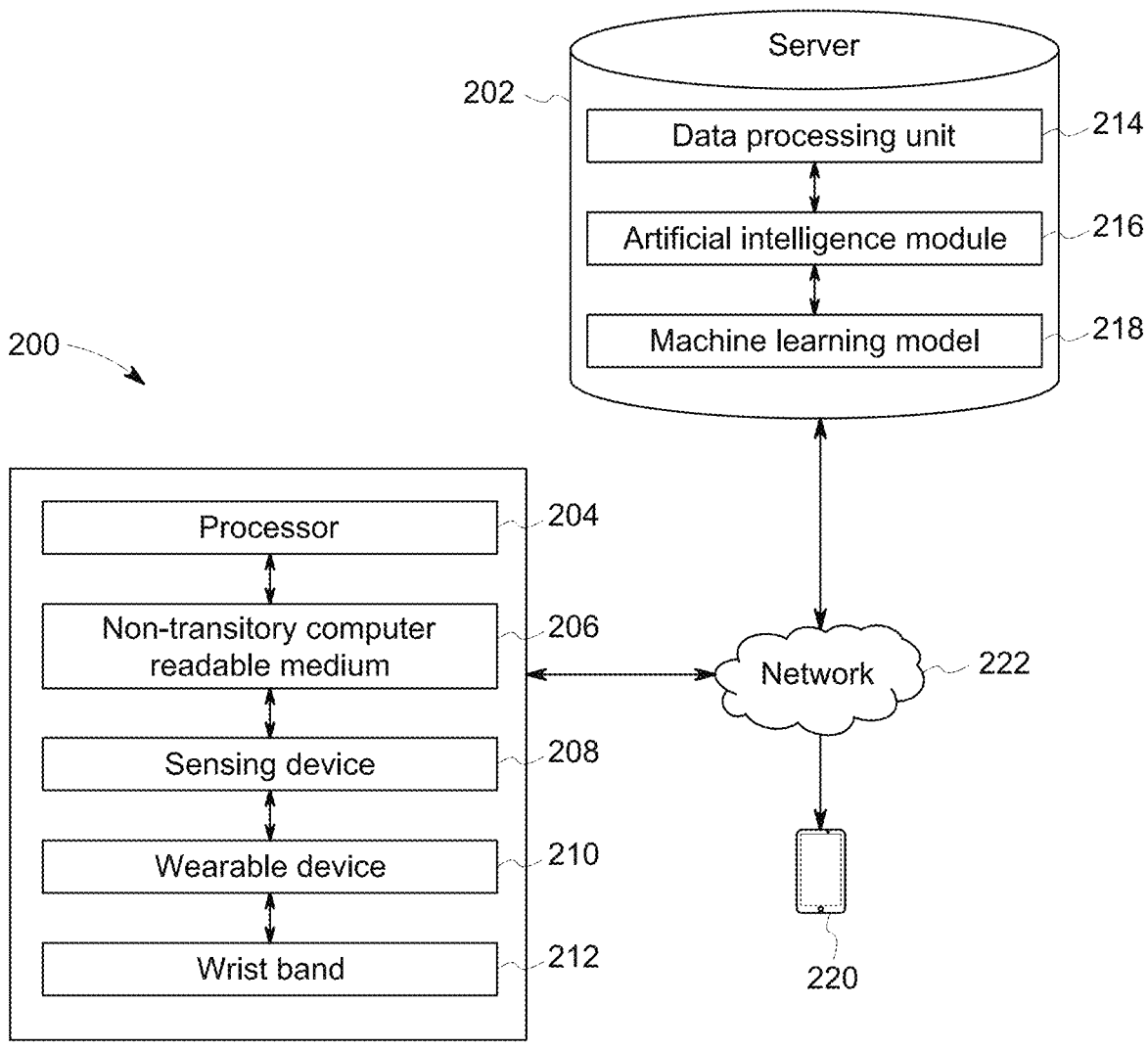

FIG. 13 illustrates a block diagram of an apparatus for monitoring vital signs of a user, in accordance with another exemplary embodiment of the invention.

Figure 14:
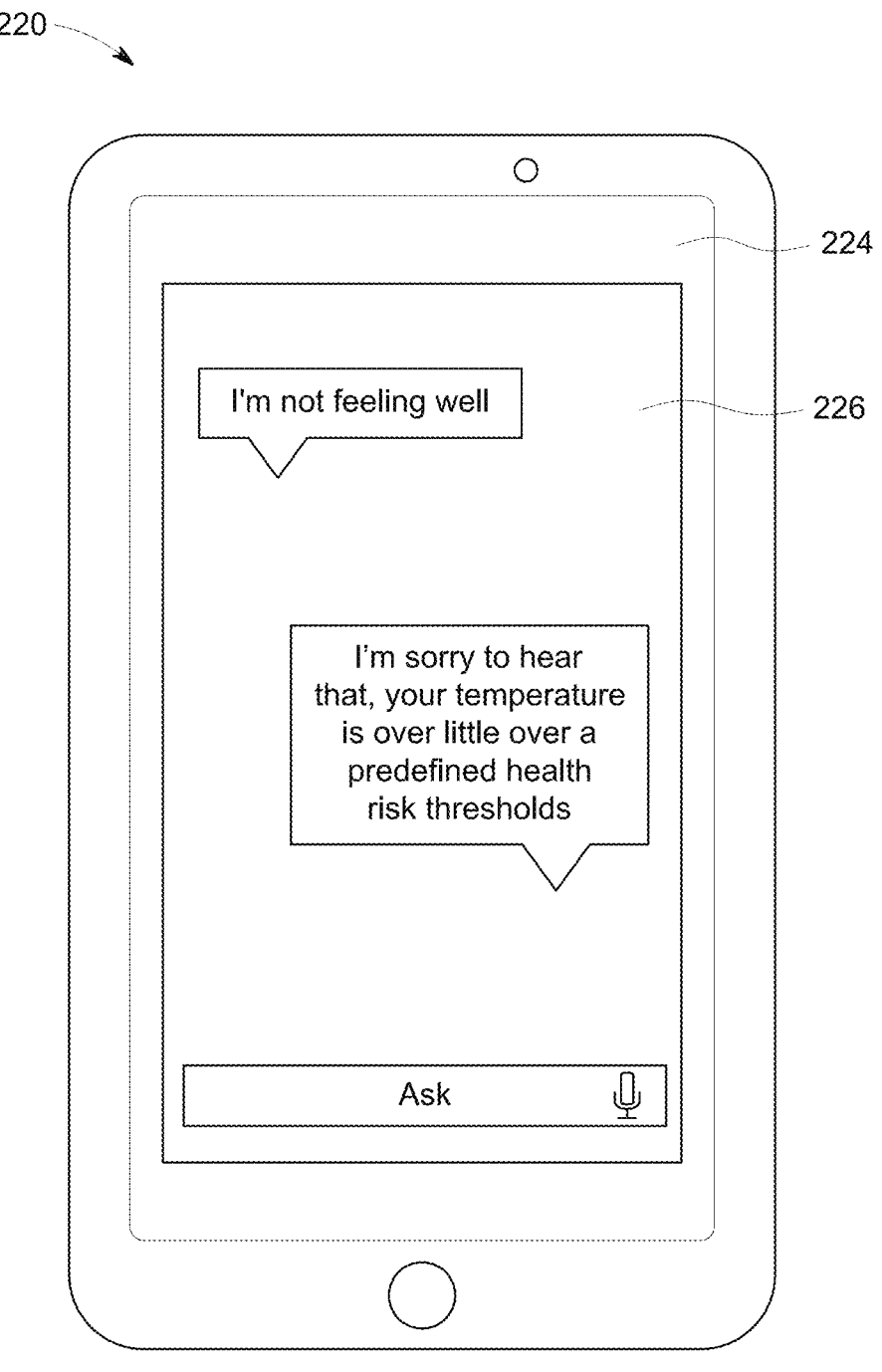

FIG. 14 illustrates a network-securing graphical user interface (GUI) is displayed on a user interface of a computing device, in accordance with another exemplary embodiment of the invention.

Figure 15:
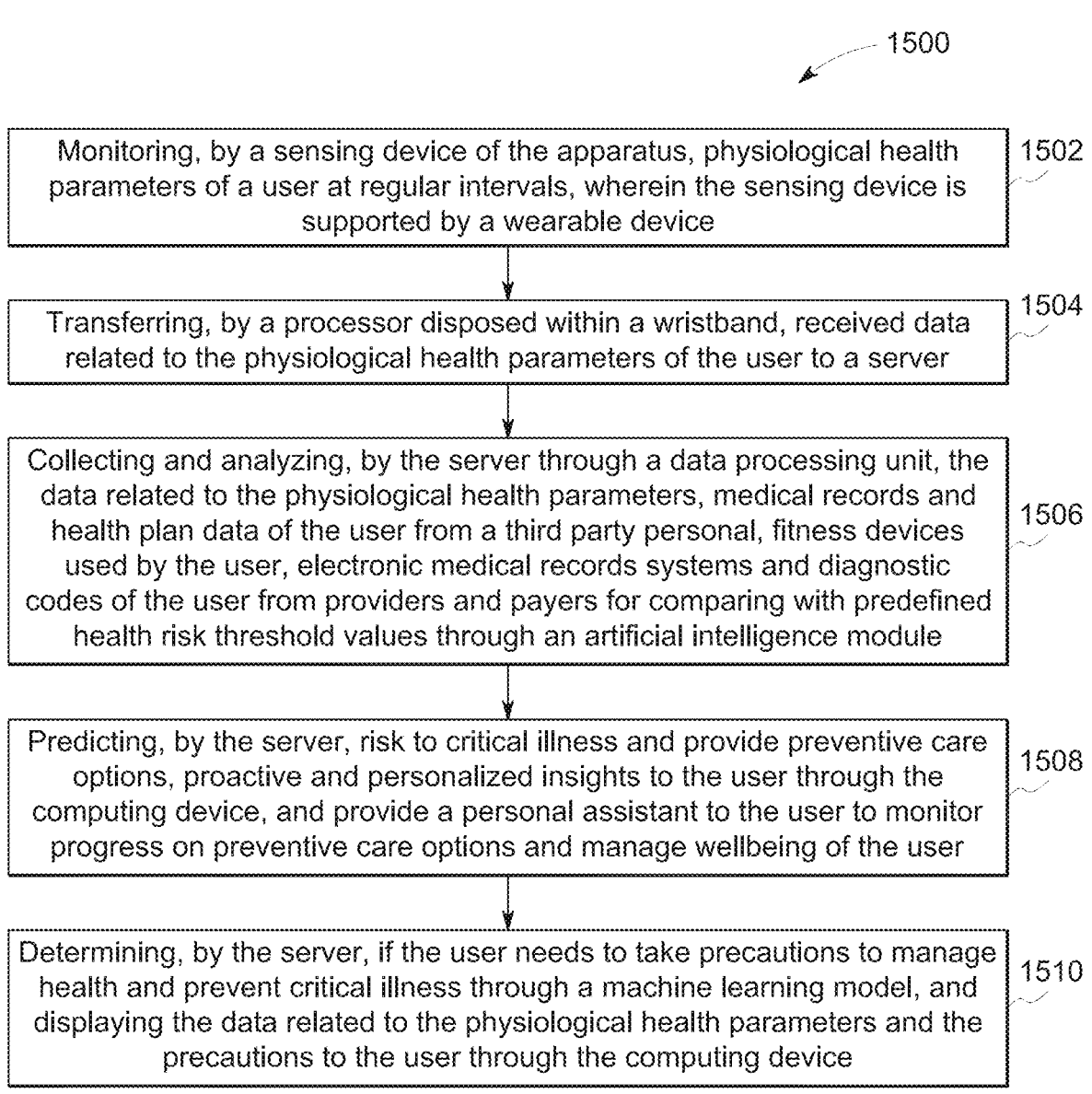

FIG. 15 illustrates a flowchart of a method for monitoring, tracking, and storing vitals data through the apparatus, in accordance with another exemplary embodiment of the invention.

DETAILED DESCRIPTION

The ability to accurately measure and track human body vital signs is critical to determining, evaluating, and improving a person's health and wellness. Additionally, accurate vital measurements are important to health care providers when determining a patient's medical needs. The use of vital sign monitors and trackers have proven to be a great tool for consumers and health care providers. Currently, there is not a device that can simultaneously track a user/patient's vital signs and share vital signs data with the user/patient, family members, and health care team. For example, existing vital sign monitors are limited to tracking body temperature only as a fever spikes or are limited to use for infants. Additionally, existing monitors do not have features capable of remote diagnosis or continuous monitoring or collecting and combining data from multiple sources including, but not limited to, personal fitness devices, electronic medical records systems, diagnostics code from payers to accurately and reliably predict risk to critical illness, improve patient outcomes and manage health.

The present disclosure solves these problems and is drawn to apparatuses, devices, systems, and methods of tracking a user's vital signs, displaying and storing the user's vital signs on a mobile dashboard or web platform, and notifying the user when vital signs are out of range. In some embodiments, the mobile dashboard or web platform allows the user to input minimum and maximum values for each vital sign and can send warnings, notifications, or alerts if the user's vital signs are outside of the inputted minimum and maximum values. In some embodiments, the mobile dashboard or web platform stores historical vital signs data that the user and other authorized third parties can access and creates seamless communication between the patient/user, the health care team, and family members. In some embodiments, the present disclosure is directed to providing a medical device that a healthcare team, including physicians, nurses, and home health aides, can use to monitor and provide care to a patient.

Figure 1:
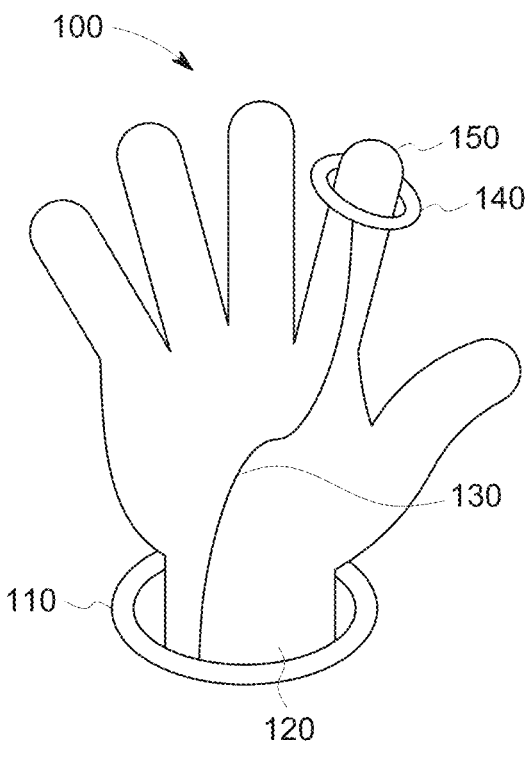
FIG. 1 is an illustration showing a configuration of an exemplary apparatus as worn by a user, according to some embodiments of the present disclosure.

In some embodiments, the apparatus of the present invention can monitor various vital signs, such as body temperature, pulse rate, oxygen levels, mental state resilience, hydration, and/or some combination of these vitals. Mental state resilience is determined based on heart-rate variability. For example, if the patient's heart rate is frequently changing, the patient will demonstrate low mental state resilience. Hydration is determined based on oxygen levels. For example, low oxygen levels correlate to low hydration, The present disclosure describes in one embodiment an apparatus and mobile dashboard or web platform and methods of use of the apparatus with the web-based application to monitor the body temperature, heart rate, average oxygen level, and body movement of a human subject. FIG. 1 is an illustration showing a configuration of an exemplary apparatus 100 as worn by a user, according to some embodiments of the present disclosure. The apparatus 100 can include a vitals sensor 150, a ring 140, a cable 130, a motherboard 120, and a wristband 110. Vitals sensor 150 can include mechanical components and/or electronic sensors that respond to body vital signs, such as body temperature, oxygen level, heart rate, and body movement. Ring 140 can be made of an adjustable material to fit the user's finger. Motherboard 120 can include mechanical and/or electrical components that store data. Vitals sensor 150 is placed within the ring 140. For most accurate vital sign measurements, the vitals sensor 140 should be placed near the pad of the index finger. Motherboard 120 can include a battery or connection port to a power source. Cable 130 can be made of a material that transfers power from motherboard 120 to vitals sensor 150. Exemplary materials include, jumper wires, aluminum electrical wires, copper electrical wires or other conductive connective wires or cables, Wristband 110 can be made of a material capable of storing motherboard 120 and connecting to jumper 1.30. Exemplary materials include, silicone, rubber, textile fabrics or other non-conductive materials.

Figure 2:
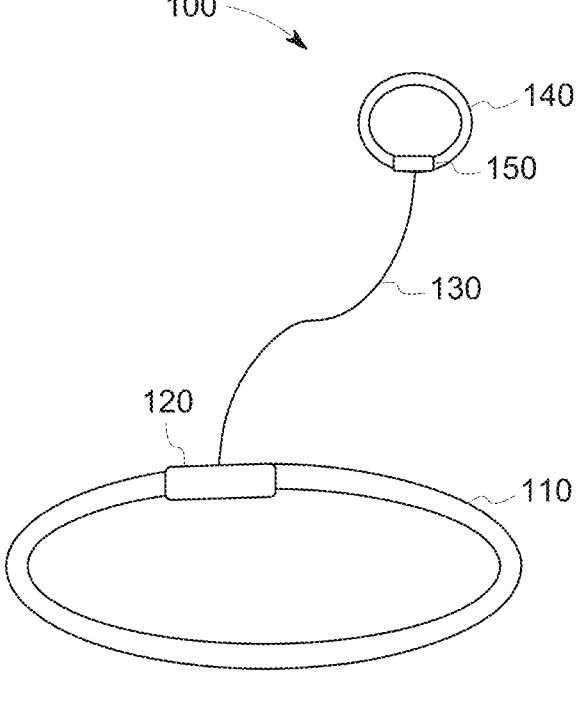
FIG. 2 is an illustrative diagram showing an exemplary apparatus according to some embodiments of the present disclosure.

FIG. 2 is an illustration showing a configuration of an exemplary apparatus 100. Vitals sensor 150 can monitor the vital signs of the user. Vitals sensor 150 collects the vitals data and sends the data to motherboard 120. Motherboard 120 sends the data to the web-based application and provides power to the sensor by sending electrical supply to the sensor. In some embodiments, motherboard 120 receives power from a computer. In some embodiments, motherboard 120 receives power from a portable power-bank. In some embodiments, motherboard 120 receives power from a battery. In some embodiments, the ring 140 may be of various sizes and materials (e.g., silicone, rubber, textile fabric, or other non-conductive material). The size of ring 140 can be adjusted to fit the size of the user's finger. In some embodiments, the wristband 110 may be of various sizes and materials (e.g., silicone, rubber, textile fabric, or other non-conductive material). In some embodiments, the jumper 130 may be of various lengths and materials. The length of jumper 130 can be adjustable based on the size of the user's hand. The jumper must be connected to the input and output ports of the motherboard and sensor in order for the motherboard to power the sensor.

Figure 3:
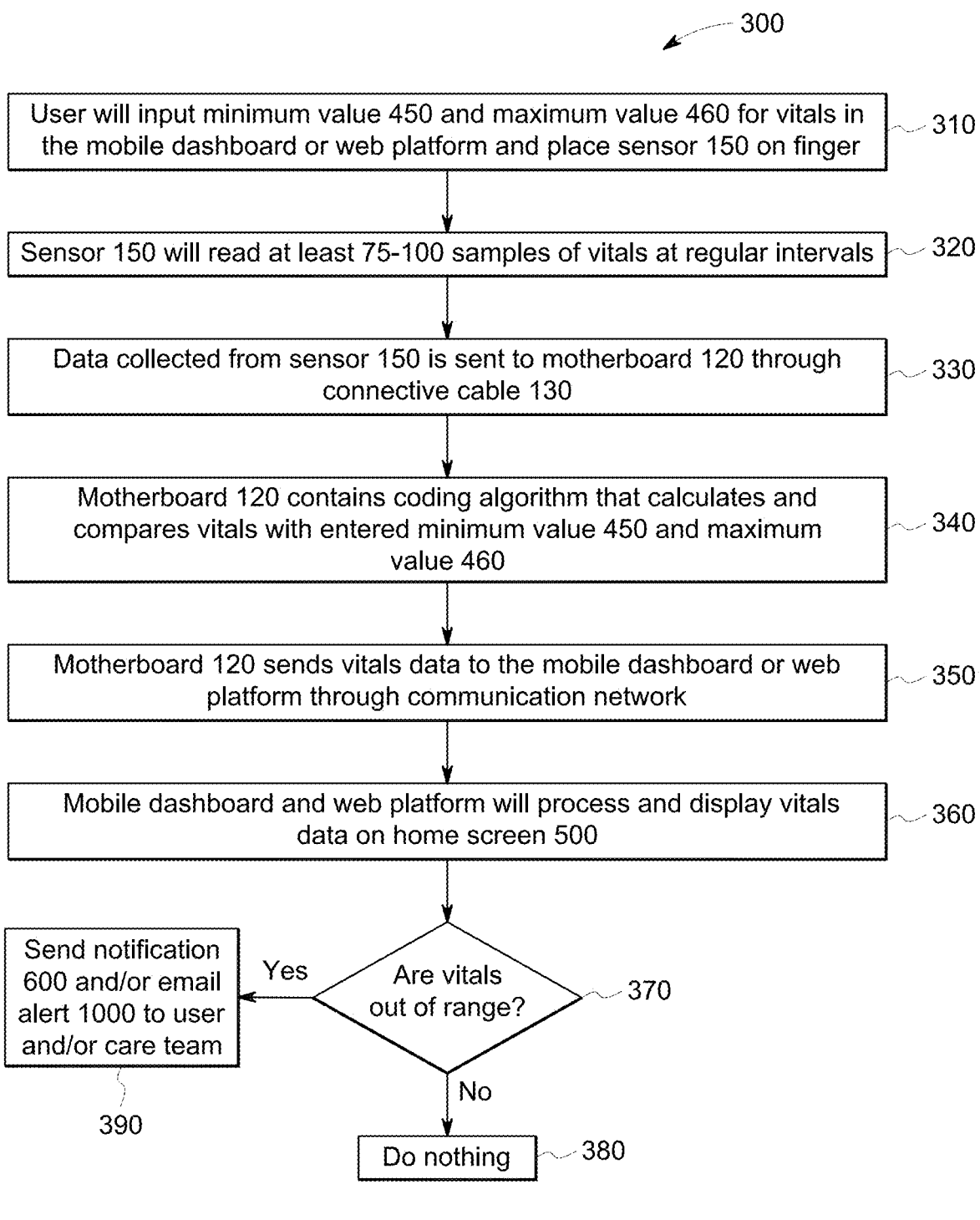
FIG. 3 is an illustrative flowchart showing the process of using the apparatus and mobile dashboard or web platform, according to some embodiments of the present disclosure.
Figure 4:
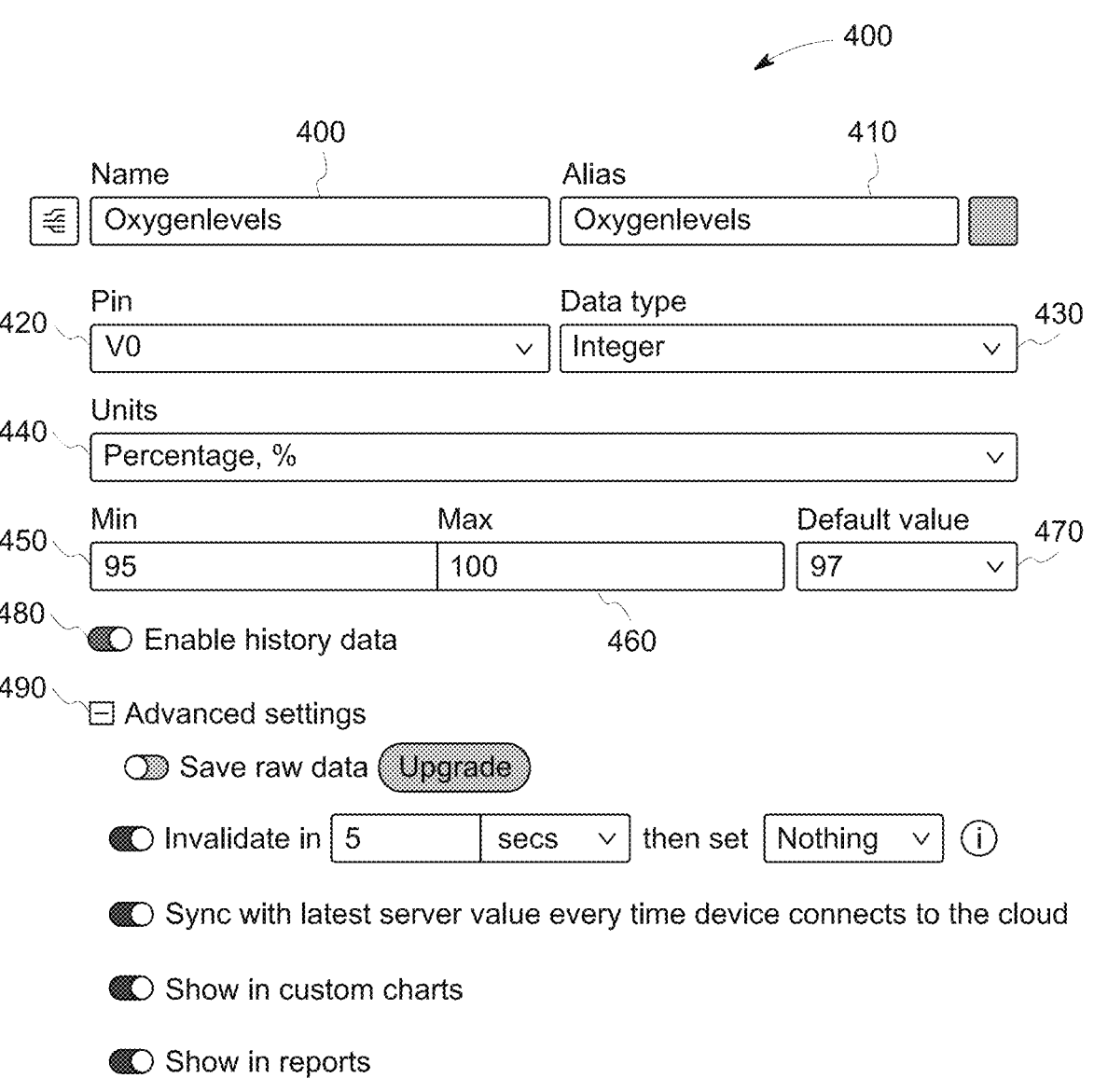
FIG. 4 is an exemplary illustration of the input screen for the user to input customizable minimum and maximum values for monitored vital signs.

FIG. 3 is an illustrative flowchart showing the process of using the apparatus 100 and mobile dashboard or web platform. The apparatus 100 can send vitals information to either/both a mobile dashboard or web platform. First, as shown in box 310, the user or authorized third party, such as a healthcare provider, will input customizable minimum vital value 450 and maximum vitals value 460 in the mobile dashboard or web platform as shown in FIG. 4 and place vitals sensor 150 on the user's finger. Next, as shown in box 320, the vitals sensor will read, for example, at least 75 to 100 samples of vitals information at regular intervals. In other examples, the vitals sensor reads 25 to 50 samples, 50 to 75 samples, or over 100 samples. In some embodiments, the vitals sensor will collect vitals data at regular intervals (e.g., 30 second, 1 minute, 90 second, and 2 minute intervals). Then, as shown in box 330, the vitals data collected from sensor 150 is sent to motherboard 120 through the connective cable 130. In some embodiments, each sample is sent sensor 150 to the motherboard 120 individually, the motherboard 120 a coding algorithm that averages the collected samples (e.g.. 75 to 100 samples). The coding algorithm within motherboard 120 then compares the average of the collected vitals data with entered minimum value 450 and maximum value 460, as shown in box 340. Then, as shown in box 350, the motherboard 120 sends vitals data to the mobile dashboard or web platform through a communication network such as, for example, cable networks, public networks (e.g., the Internet), wireless networks, cellular networks, metropolitan area networks (MANs), wide area networks (WANs), local area networks (LANs), personal area networks (PANs), Bluetooth connection, and Wi-Fi connections. Then, as shown in box 360, the mobile dashboard or web platform will process and display the vitals data on home screen 500. The mobile dashboard or web platform will analyze whether the vitals are out of range, as shown in box 370. The mobile dashboard or web platform will do nothing when vitals are not out of range, as shown in box 380. Otherwise, as shown in box 390, the mobile dashboard or web platform will send notification 600 or email alert 1000 to the user and/or care team when vitals are out of range.

In some embodiments, the user can manually track and monitor their vitals. The patient or user can use the mobile dashboard or web platform to refresh their vitals data on-demand. The apparatus monitors the vitals multiple times over a period of time (e.g., in 30 second, 1 minute, 90 second, or 2 minute intervals) and the mobile dashboard or web platform will display the most recently monitored data on home screen 500.

FIG. 4 is an illustration depicting the input screen for the user of the apparatus 100, or an authorized third party such as a healthcare provider, to input customized, personal vital sign information. The input screen displays the pre-populated name of the vital sign 400 and alias of the vital sign 410. The input screen also displays the pre-populated unique identifier 420 assigned to the vital sign (e.g., PIN value). In some embodiments, the unique identifier 420 is a particular symbol used to identify the individual vital sign that the system determines and cannot be customized by the user. The input screen also displays the data type 430 (e.g., integer). In some embodiments, the data type 430 is determined by the system, cannot be customized by the user, and identifies the type of data the system is collecting. The input screen also displays the units 440 (e.g., percentage, %). In some embodiments, the units 440 is determined by the system, cannot be customized by the user, and identifies the type of unit of data type 430 collected by the system. In some embodiments, the input screen will have an option to input a minimum value 450 and maximum value 460 for the vital sign. In some embodiments, the input screen will also have a pre-populated default value 470 based on average values of the vital sign. In some embodiments, the input screen will have a toggle for the user to enable history data 480 and advanced settings 490. In some embodiments, enabling history data 480 allows the mobile dashboard and/or web platform to store historical vitals data. An example of advanced settings 490 includes displaying "Nothing" or "No Data" when the mobile dashboard or web platform has not received data in a set amount of time (e.g., 1 minute). Another example of advanced settings 490 includes syncing with latest server value every time device connects to the cloud. When this setting is turned on, a device that has been offline will retrieve the latest value collected from the sensor 150 when the system turns back online. The motherboard 120 will then collect data regularly as shown in FIG. 3. Another example of advanced settings 490 includes showing vitals data in custom charts and reports for the user, health care team and/or doctor to see vitals data over a period of time. In some embodiments, the collected vitals data from box 330 can be plotted in a graph to show the patient's progress related to that particular vital sign. In some embodiments, the collected vitals data from box 330 can be used to show improvement or decline related to the particular vital sign, as well as the rate of acceleration or deceleration of the improvement or decline. In some embodiments, the collected vital signs from box 330 can be used to provide an overview of a patient's vital signs mapped against the patient's circadian rhythm. Over time, if the vital signs are not following the patient's circadian trend, the system can alert the health care team of possible sleep disturbance.

Figure 5:
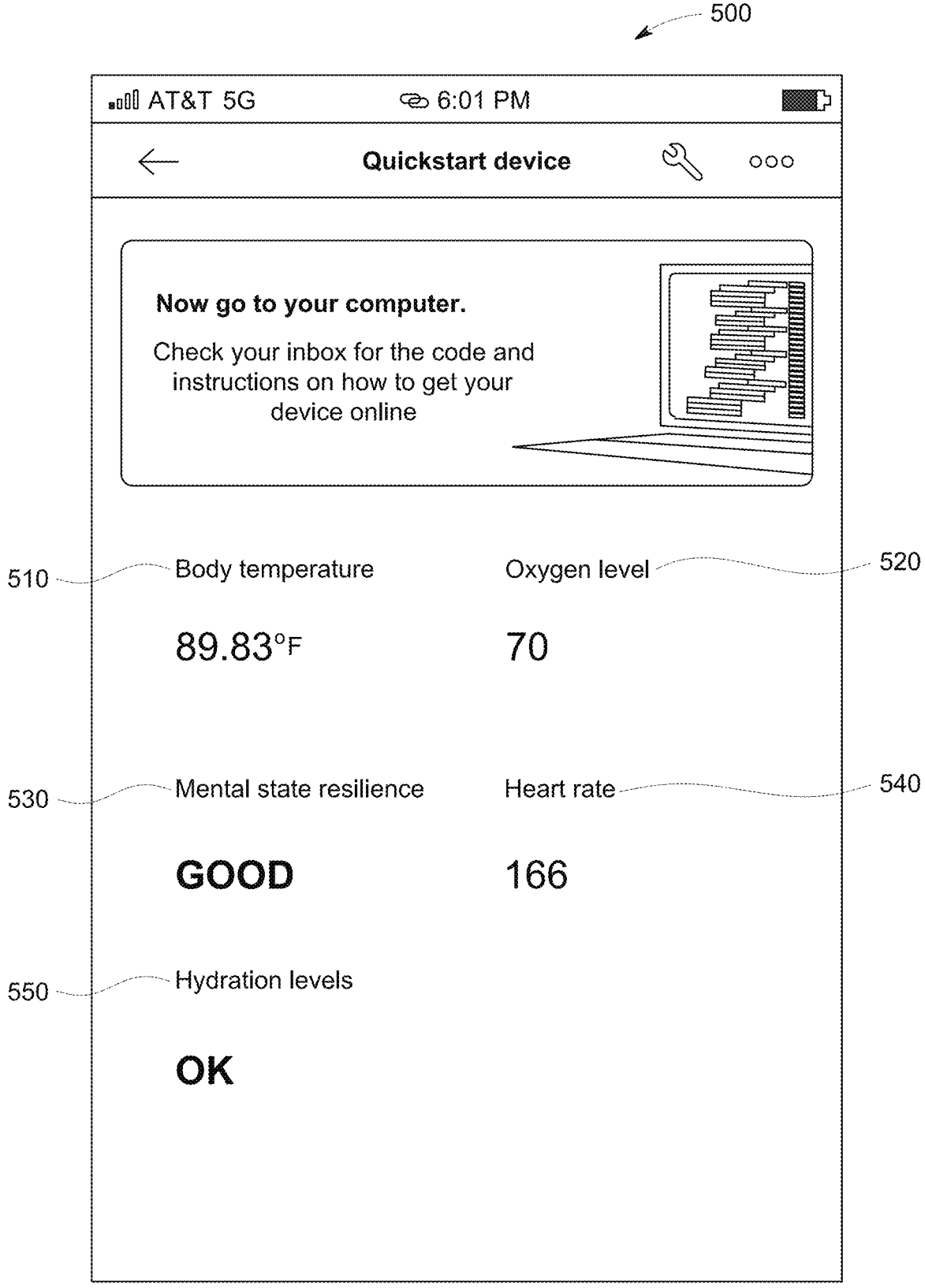
FIG. 5 is an exemplary illustration of the mobile dashboard platform.

FIG. 5 is an illustration depicting an exemplary home-screen for the mobile dashboard. In some embodiments, the home screen 500 will display body temperature 510, oxygen level 520, heart rate 530, mental state resilience 540, and hydration levels 550. The data shown on this screen can be the last sample collected by vitals sensor 150. In other embodiments, it can display the average value of collected samples over the previous minute, hour, 6-hour period, 12-hour period, or day. A display reading of "GOOD" for mental state resilience indicates minimal or no variability in heart rate. A display reading of "POOR" for mental state resilience indicates abnormal variability in heart rate. A display reading of "OK" for hydration levels indicates regular body temperature and regular oxygen levels. A display reading of "POOR" for hydration levels indicates high body temperature and low oxygen levels.

Figure 6:
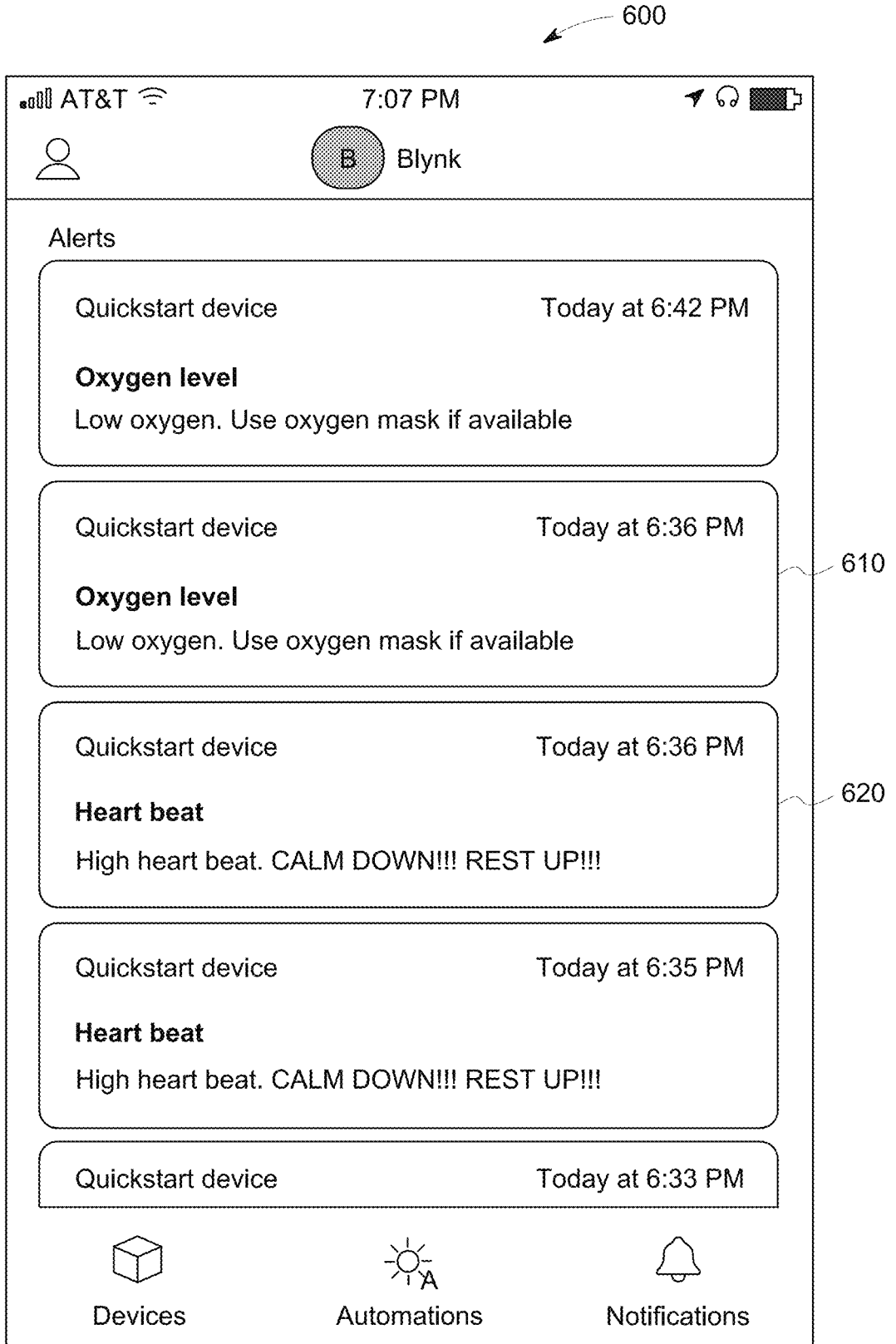
FIG. 6 is an exemplary illustration of mobile notifications when vital signs are outside of the user designated minimum and maximum range of the monitored vital signs.

FIG. 6 is an illustration depicting an exemplary display of mobile device notifications 600 in the mobile dashboard. Notifications are sent to the mobile dashboard when vital signs are outside of the inputted range. Exemplary notification for low oxygen level 610 displays an alert, such as "Oxygen Level: Low Oxygen Use Oxygen Mask if available." Exemplary notification for high heart rate 620 displays an alert, such as "Heart Beat: High heartbeat. Calm down! Rest up!" In some embodiments, a notification is sent when oxygen levels drop for over 30 seconds, one minute, two minutes, five minutes, ten minutes, or longer. In some embodiments, a notification is sent when hydration levels decrease over the course of 10 minutes, 20 minutes, 30 minutes, 40 minutes, 50 minutes, 60 minutes, or longer. In some embodiments, a notification is sent immediately when heart rate variability indicates atrial fibrillation or other severe cardiac conduction abnormality.

Figure 7:
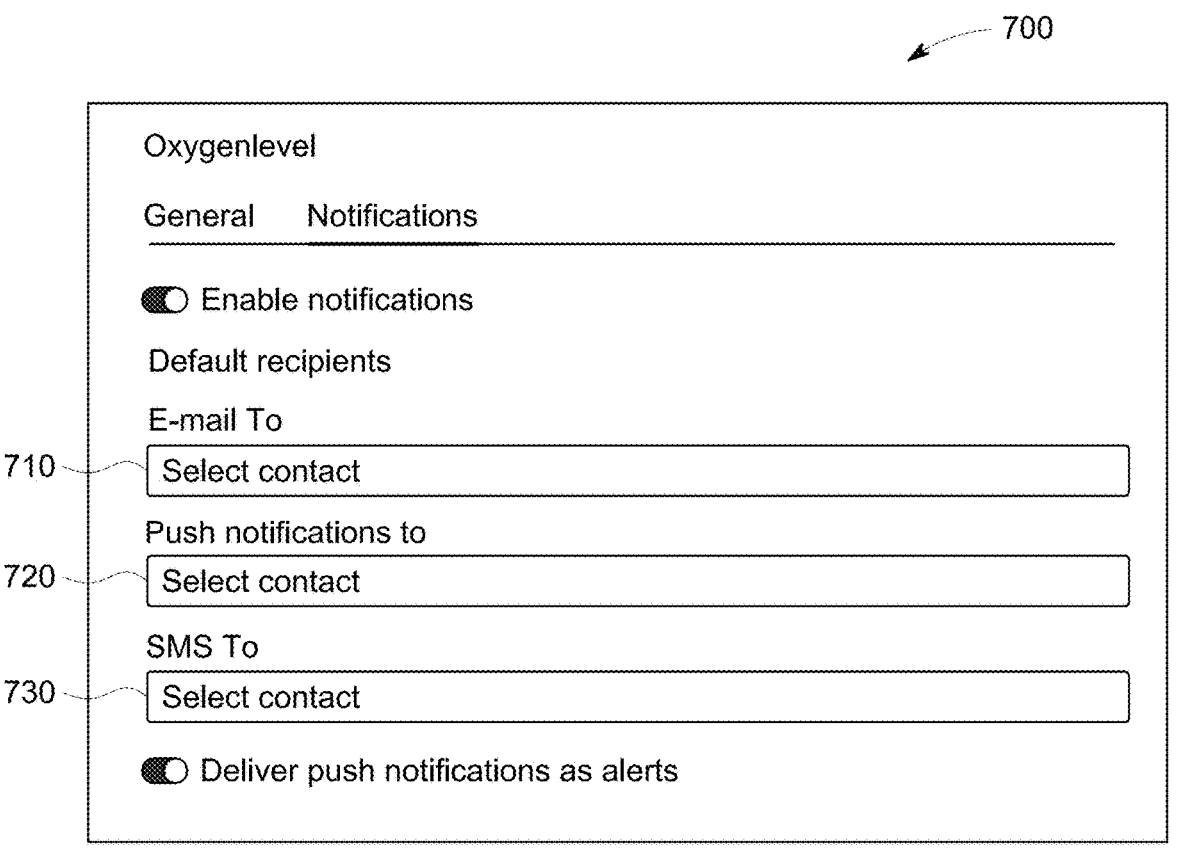
FIG. 7 is an exemplary illustration of the mobile dashboard notification enablement screen.

FIG. 7 is an illustration depicting an exemplary input screen for the user or authorized third party to set up notification alerts 600 when the user's vital signs are out of the minimum value 450 and maximum value 460 range for a designated period of time the user or authorized third party inputted in the display of FIG. 4. In some embodiments, the input screen for setting up notifications includes a text box to input email contact information 710 for the user and authorized third parties to receive notifications. In some embodiments, the input screen for setting up notifications includes a text box to input mobile application push notifications 720 for the user and authorized third parties to receive notifications. In some embodiments, the input screen for setting up notifications includes a text box to input SMS text contact information 730 for the user and authorized third parties to receive notifications.

FIG. 8 is an illustration depicting an exemplary input screen for the user or authorized third party to grant access to the user's vital sign information to other individuals. In some embodiments, the input screen includes a text box for the authorized third party's email address 810, the authorized third party's name 820, the authorized third party's phone number 830, and the role or relation of the authorized third party to the user 840. In some embodiments, the role of the user is "admin" and the role of other authorized third party's is "user".

FIG. 9 is an illustration depicting an exemplary input screen for the user to customize the warning, alert, and notification messages that the user and authorized third parties will receive. In some embodiments, the name of the vital sign 910 and the event code 920 is pre-populated. In some embodiments, the type of alert 930 can be selected from options including "info," "warning," "critical," and "content" In some embodiments, the input screen for customizing warning and notification messages will include a text box for a custom description 940. For example, this is where the message shown in FIG. 6, "CALM DOWN!!! REST UP!!! can be included. In some embodiments, a text box is available for the user to input the limit 950 of messages triggered to avoid excessive notifications if the associated vital sign is out-of-range for a long period of time. For example, if the user's oxygen level is low for a long period of time, the system's default setting is to send an alert or notification for each collection of samples sent from the sensor 150 to the motherboard 120. The limit 950 will reduce the number of alerts or notifications sent to the designated amount (e.g., 1 notification per minute) even if there are multiple readings that are out of range within that designated time period.

FIG. 10 is an illustration depicting an exemplary email alert the user or authorized third party will receive. In some embodiments, the name of the vital sign 1010, the custom alert or message 1020, the option to open the notification in the app or mute notifications 1030, and the date and time of the notification 1040 will appear in the email. The email alert will depict the customized message the user entered in the input screen of FIG. 9.

FIGS. 11A-11B illustrate a ring extension 1100 of the apparatus 100. Ring extension 1100 is a different configuration of the apparatus 100. Ring extension 1100 only includes the ring 140, which holds the sensor 120 and the motherboard 150. In some embodiments, the ring extension 1100 includes a hidden connective cable 130 within the material of ring 140. In some embodiments, the sensor 120 sends data to the motherboard 150 through the material of ring 140. FIG. 11A depicts an inside view of the ring extension, where the motherboard 120 is visible. FIG. 11B is a side view of the ring extension, where the motherboard 120 and the vitals sensor 150 are visible on the inside of the ring.

FIGS. 12A-12B illustrate a bracelet extension 1200 of the apparatus 100. Bracelet extension 1200 is a different configuration of the apparatus 100. The bracelet extension 1200 only includes wristband 110, which holds sensor 120 and the motherboard 150. In some embodiments, bracelet extension 1200 includes a hidden connective cable 130 within the material of the wristband 110. In some embodiments, the sensor 120 sends data to the motherboard 150 through the material of wristband 110. FIG. 12A is an outside view of the bracelet where the motherboard 120 is visible. FIG. 12B is a side view of the bracelet wearable, where motherboard 120, the vitals sensor 150, and bracelet adjustment clip 1210 is visible.

Patients can use any one of devices 100, 1100 or 1200 to monitor their vitals on-demand. Significant or critical changes to vitals can occur in between active vitals readings. Using the present invention, a patient can monitor their own vitals at any time and from any location, as long as the patient is wearing the device. If the patient's vitals are out of the designated normal range for a designated period of time, the application will send an alert to the patient. This allows the patient to quickly respond and take the necessary actions to return to their normal range of vitals. Based on the unique minimum and maximum vital sign values, the patient has access to health indicators like the mental state resilience and the hydration levels provided by the application. This will prevent patients from suffering from catastrophic illnesses, such as heart attacks, as the invention will be able to detect early symptoms and warn the patient.

If given access by the patient, doctors can use the invention to monitor their patients" vital signs. If granted access by the patient to the patient's vital sign information and patient's health data from multiple sources, doctors can give more accurate diagnoses and treatment plans. Doctors can also provide patients with well-informed recommendations based on the patient's vital readings and holistic view of patient's health data from multiple sources. The invention will also improve concierge medicine because it will help build stronger connections between the patient and doctor. Because the doctor can view the patient's real-time vital sign information at any time from any location and get a holistic view of patient's health data, the doctor will be able to provide more personalized care to the patient. The mobile application captures the historical data and enables doctors to view historical trends, which can increase efficiency and the accuracy of the diagnosis and treatment in telehealth and home health. With access to historical patient vital data and historical data from multiple sources, doctors in the concierge medicine industry will have immediate information related to the patient, improving the efficiency and effectiveness of concierge medicine. Additionally, the patient can directly share the vitals data and data from multiple sources with their doctor. If any monitored vitals are out of range, a notification will also be sent to the doctor so they can offer any treatment or care if necessary.

Nurses typically check a patient's vitals before the doctor checks on the patient. However, when nurses enter the treating room, patients may be carrying a contagious infection or disease. Nurses are at a high risk of infection due to the close proximity in which they care for the patient. The present invention can help solve this issue as the nurse can use the product to remotely and accurately monitor the vitals in real time. They can also view a patient's historical data, patient's medical data from multiple sources, predictions for risk to critical illness, preventive care options which gives the nurse important information about the patient and provides the nurse with information to share with doctors, if necessary. Authorized nurses will also receive a notification if one of the vitals are out of range so that corrective actions can be taken. With this invention, nurses will be able to care for all their patients without risking their own health.

When individuals contract diseases, their family members and loved ones are often the people who care for them. For children especially, family members and other loved ones need to come into close contact with sick family members to monitor their vital measurements. Because common diseases are contagious, this puts the caretaker at a high risk of contracting the disease. The present invention can be used so that family members and caretakers preserve their own health and can simultaneously monitor the family members' vitals in real-time.

Additionally, the application provides notifications when the patient's vitals are out-of-range, which makes providing care for the patient easier and more efficient for the caretaker.

The present invention is a unique solution that is targeted towards the amalgamation of the care team (i.e., doctors, nurses, care team) by providing seamless communications and accurate vital sign information, The invention also uniquely predicts risk to critical illness based on vital sign information and combined patient health data collected from multiple sources and recommends preventive care options. The care team will highly benefit from because they can each monitor vitals and patient's health data from a remote location without risking exposure to the sick patient. The patient has the sole discretion to share their information with who they choose to have access to the vitals. Additionally, the web-based application displays all the historical data in real time for the care team to use and a holistic view of patient's medical data from multiple sources with predictions for risk to critical illness.

FIG. 13 refers to a block diagram of an apparatus 200 to monitor, track, and store vital signs. The apparatus 200 comprises a sensing device 208, a wearable device 210, and a wristband 212. The computing device 220 is configured to provide proactive insights for early risk detection, preventive recommendations to reduce health risks, and personalized care based on individual patient data. The apparatus 200 is in communication with a computing device 220 through a server 202 via a network 222. The server 202 comprises a data processing unit 214, an artificial intelligence module 216, and a machine learning model 218. In one embodiment, the apparatus 200 is configured to wirelessly communicate with the server 202 and computing devices 220 through the network 222. In one embodiment herein, the network 222 can be a wireless communication infrastructure, which offers the users flexibility and convenience when interacting with the apparatus 200.

In one embodiment, the sensing device 208 is configured to monitor data related to physiological health parameters of a user at regular intervals. The data related to the physiological health parameters comprises, but is not limited to, glucose levels and blood pressure. In one embodiment, the wearable device 210 is configured to be worn on at least one finger of a user's hand. The wearable device 210 is configured to support the sensing device 208. The wristband 212 is configured to allow the user to wear on a wrist. The wristband 212 comprises a processor 204 and a non-transitory computer readable medium 206 for storing program instructions that are executable by the processor 204.

In one embodiment, the sensing device 208 is in communication with the computing device 220 through the network 222. The server 202, the processor 204, the sensing device 208, the wearable device 210, and the wristband 212, the computing device 220 is communicatively coupled to the network 222 through connections. The connections can be wired connections, wireless connections, or a combination thereof. The network 222 acts as a communication that allows the computing device 220 to interact with the other components of the apparatus 200, thereby facilitating the exchange of data, commands, and information.

In one embodiment, the network 222 can be any multi-hop network that covers regions, countries, continents, or a combination thereof. Examples of the network 222 can include a cellular network such as a 3G network, a 4G network, a long-term evolution (LTE) network, a sonic communication network, a satellite network, a wide area network such as the Internet, or a combination thereof. In one embodiment herein, the network 222 can be a wireless communication infrastructure, which offers the user flexibility and convenience when interacting with the apparatus 200. This wireless connectivity enables the user to access the apparatus 200 from various locations, without being tethered to a fixed physical connection.

In one embodiment herein, the network 222 can be, but not limited to, Local Area Network (LAN), Cellular Network, Wide Area Network (WAN), Intranet, Virtual Private Network (VPN), and wireless networks that use radio frequency (RF) or infrared (IR) technology to transmit data without the need for physical cables, thereby providing mobility and flexibility. The versatility of the network 222 ensures that the computing device 220 can seamlessly connect to the server 202, thereby enabling the user to access the apparatus's functionalities and resources from a variety of locations and devices. This wireless connectivity enhances the overall accessibility and convenience of the apparatus 200 for the user.

In one embodiment herein, the computing device 220 represents any electronic device that the user can utilize to interact with the apparatus 200. The computing device 220 can be, but not limited to, a smartphone, a laptop, a tablet, a personal computer, or any other suitable electronic device. The computing device 220 serves as the user's gateway to accessing and interacting with the apparatus 200.

In one embodiment, the computing device 220 is configured to receive the data related to the physiological health parameters from the sensing device 208. The computing device 220 is configured to receive medical records and health plan data of the user from a third party personal, fitness devices used by the user, electronic medical records systems and diagnostic codes of the user from providers and payers. The computing device 220 is configured to transmit the data related to the physiological health parameters, the medical records and the health plan data to the data processing unit 214 of the server 202. In one embodiment, the data processing unit 214 is configured to further receive real-time physiological data from the wearable device 210 continuously. In one embodiment, the data processing unit 214 is configured to receive medical records, health plan data from third party fitness devices used by the user, electronic medical records systems and diagnostic codes of the user from providers and payers.

In one embodiment, the server 202 is configured to analyze the data related to the physiological health parameters, the medical records, and the health plan data through the data processing unit 214. In a preferred embodiment, the data related to the physiological health parameters, the medical records, and the health plan data are compared with predefined health risk threshold values through the artificial intelligence module 216. In some embodiments, the server 202 is configured to utilize large language models (LLMs) to provide transformative options. In some embodiments, the server 202 is configured to a self-attention mechanism to analyze significant numerical values through the data processing unit 214.

In an exemplary embodiment, the AI module 216 comprises a domain specific large language model (LLM) uniquely configured for medical analysis through interpretation and processing of multi-modal health data. Referring to FIG. 16, the LLM 301 continuously ingest, process, and reason over streaming training data inputs 302. This includes real-time data from wearable devices, API key, structured and unstructured files comprising EMRs, familial medical history, and clinical observations from the care team. The data ingestion pipeline 303 captures and delivers the data as it is generated, ensuring the model has access to the most current and contextually relevant information.

The AI module 216 leverages a cache-augmented generation 304 mechanism, allowing the model to access and respond using both pre-trained knowledge and freshly ingested facts. This hybrid capability ensures the LLM 301 to provide advice that is both contextually informed and medically accurate. Additionally, the model operates within a continuous learning architecture 305 that enables real-time updates to inference engine 306 without requiring full model retraining. Modular components within the system allow fine-tuning of ML model 307 weights based on recent data trends and biases, wherein the fine-tuned model processes the input 308 and delivers an accurate output 309 in the computing device 220, thereby improving efficiency and responsiveness. In some embodiments, the AI module 216 further employs a self-attention mechanism via the data processing unit 214 to identify and prioritize clinically significant numerical values from heterogeneous data sources. This enables precise pattern recognition, anomaly detection, and risk stratification in dynamic patient scenarios.

The apparatus 100 through AI module 216, can perform medical-grade inferencing that would not be possible for a human practitioner alone. The LLM 301 implemented within the AI module 216 ingests millions of data points within minutes and provide analysis and diagnostic recommendations at a scale and speed unattainable by the human brain, which is limited in both data bandwidth and continuity. Furthermore, unlike human medical professionals who are subject to availability constraints, the AI module 216 provides uninterrupted 24/7 responsiveness, enhancing patient safety and consistency of care.

In some embodiments, the server 202 is configured to utilize reinforcement learning that is applied to generate outputs customized to the user. In some embodiments, the server 202 provides proactive insights by continuously monitoring and analyzing health trends, enabling early risk detection for conditions such as cardiovascular diseases, diabetes, or respiratory disorders. In some embodiments, the server 202 utilizes LLMs to generate preventive recommendations based on identified risk factors, suggesting lifestyle changes, medication adjustments, or early medical interventions to mitigate potential health threats.

In some embodiments, the server 202 deliver personalized care by tailoring insights and recommendations to the individual's health history, real-time physiological data, and external health records, ensuring a patient-centric approach to disease prevention and management.

In one embodiment, the server 202 utilizes LLMs to predict risk to critical illness and generate a health risk assessment. The server 202 utilizes LLMs to provide preventive care options, proactive and personalized insights to the user through the computing device 220. The server 202 utilizes LLMs to provide a personal assistant to the user to monitor progress on preventive care options and manage wellbeing of the user through the computing device 220.

In one embodiment, the computing device 220 is configured to enable the user to engage with the system's functionalities and capabilities through a user interface 224 (as shown in FIG. 14). The user interface 224 is a crucial component of the computing device 220, which allows the user to input commands, and receive information from the apparatus 200 and the server 202. The user interface 224 can be, but not limited to, a touch screen, a keyboard, a mouse, voice recognition modules, gesture recognition sensors, and virtual reality interfaces. The versatility of the user interface 224 ensures that the users can engage with the apparatus 200 and the server 202 in a manner that is most intuitive and comfortable for the users, thereby catering to a wide range of user preferences and accessibility needs.

FIG. 14 refers to a network-securing graphical user interface (GUI) is displayed on the user interface 224 of the computing device 220, according to one or more embodiments. The network-securing GUI may be rendered through an application 226. In one embodiment, the application 226 includes, but is not limited to, a web browser application or a mobile application. In some embodiments, the mobile application may be implemented as a standalone application. It should be understood by one of ordinary skill in the art that the methods disclosed herein can also be implemented as a software development kit (SDK) configured for integration into the code stack of a mobile or web platform.

In one embodiment, the server 202 utilizes LLMs to determine if the user needs to take precautions to manage health and prevent critical illness through the machine learning model 218. The data related to the physiological health parameters and the precautions are displayed to the user through the computing device 220. In one embodiment, the machine learning model 218 is a k-nearest neighbors (KNN) model, which is configured to classify user health states and determine the preventive care options. The preventive care options comprise, but are not limited to, dietary changes, exercise regimens, and medication reminders. In a preferred embodiment, the server 202 utilizes LLMs to transmit the health risk assessment to the mobile or a web platform of the computing device 220.

In one embodiment, the server 202 utilizes LLMs to send one or more alerts to the user and a healthcare provider in response to detection of abnormal vital signs, when the predefined health risk thresholds are exceeded. The server 202 utilizes LLMs to generate at least one progress report based on the physiological health parameters for the user and share through the computing device 220. The server 202 utilizes LLMs to generate charts and graphs with timelines to visualize physiological health parameters and display them through the computing device 220.

In one embodiment, the computing device 220 is configured to display real-time health insights and preventive care options to the user and transmit progress reports to the care team (i.e., doctors, nurses, care team). In one embodiment, the preventive care options comprise, at least one of dietary changes, exercise regimens, or medication reminders.

In an exemplary embodiment, the user is allowed to input a query, such as "I'm not feeling well" through the network-securing GUI via the user interface 224 of the computing device 220. The network-securing GUI may be rendered through the application 226. The data processing unit 214 receives the query from the computing device 220 through the network 222. The data processing unit 214 utilizes LLMs to process the query internally along with the health history, the real-time physiological data, the external health records, the medical records and the health plan data of the user. The data processing unit 214 utilizes LLMs generates a response based on the query, the health history, the real-time physiological data, the external health records, the medical records and the health plan data, and the generated response is displayed on the user interface 224 of the computing device 220 for review. For instance, the data processing unit 214 utilizes LLMs provide an output, such as "I'm sorry to hear that, your temperature is over little over the predefined health risk thresholds" through the user interface 224 of the computing device 220. The data processing unit 214 utilizes LLMs responds with an analysis based on temperature readings over time, suggesting potential causes or recommending further actions.

In one embodiment, the data processing unit 214 utilizes LLMs to generate preventive recommendations, and explanations for the symptoms based on recent trends, user's condition. For example, possible causes such as, infection, or anxiety, environmental conditions, dehydration, or stress are displayed through the user interface 224 of the computing device 220.

In an exemplary embodiment, the network-securing GUI is configured for the accessing the apparatus 200 through the user interface 224 of the computing device 220. The network-securing GUI comprises a grid layout containing one or more icons. A text box below the grid provides recommendations based on articles and frequent questions, suggesting at least top five topics for users to explore. The network-securing GUI design indicates that the user can access health-related information and personalized recommendations.

In one embodiment, the apparatus 200 integrates real-time and historical data from the sensing device 208, the wearable device 210, the wristband 212, and electronic medical records (EMR) systems, and diagnostic codes from payers to provide a holistic and precise prediction of critical illnesses, preventive care strategies, and healthcare insights. The incorporation of multiple reliable data sources enhances the accuracy and reliability of predictions. Further, the apparatus 200 focuses on critical illness prediction.

In one embodiment, the LLMs operate as an AI-powered personal assistant, interpreting health data collected from multiple data sources, providing personalized recommendations, and assisting with preventive care options based on real-time inputs from the sensing device 208, the wearable device 210, and the wristband 212. The apparatus 200 includes an interactive, conversational AI-powered personal assistant designed to assist patients in managing their health proactively through daily task lists and reminders. The AI-powered personal assistant reduces the burden on caregivers and family members by allowing patients to grant them access to their care schedules, enabling real-time tracking.

In one embodiment, the apparatus 200 includes a proprietary algorithm capable of assessing a patient's mental state resilience and hydration levels. The apparatus 200 enables the predefined health risk threshold values for vital parameters, acknowledging that normal ranges vary among individuals. Notifications are triggered based on the predefined health risk threshold values, and the AI-powered personal assistant integrates the predefined health risk threshold values for vital parameters into predictions and personalized health insights, enhancing precision in health monitoring.

In one embodiment, the apparatus 200 integrates multiple physiological parameters that include, but are not limited to, the body temperature, average oxygen level, glucose levels, blood pressure, heart rate, mental state resilience, hydration levels, and body movement, into the wearable device 210, providing a comprehensive, all-in-one health monitoring solution patients.

FIG. 15 refers to a flowchart 1500 of a method for monitoring, tracking, and storing vitals data through the apparatus 200, in accordance with another exemplary embodiment of the invention. At step 1502, the sensing device 208 monitors the physiological health parameters of a user at regular intervals. The sensing device 208 is supported by the wearable device 210. At step 1504, the processor 204 disposed within the wristband 212 transfers received data related to the physiological health parameters of the user to the server 202 via the network 222. At step 1506, the server 202 collects and analyzes the data related to the physiological health parameters, the medical records and the health plan data of the user from a third party personal, fitness devices used by the user, electronic medical records systems and diagnostic codes of the user from providers and payers through the data processing unit 214 for comparing with the predefined health risk threshold values through the artificial intelligence module 216. At step 1508, the server 202 predicts risk to critical illness and provide preventive care options, proactive and personalized insights to the user through the computing device 220, and provide a personal assistant to the user to monitor progress on preventive care options and manage wellbeing of the user. Further, at step 1510, the server 202 determines if the user needs to take precautions to manage health and prevent critical illness through the machine learning model 218, and displaying the data related to the physiological health parameters and the precautions to the user through the computing device 220.

What is claimed is:

1. An apparatus for monitoring, tracking, and storing physiological data of a user, comprising:
   a wearable device configured to be worn on at least one finger of a user's hand, which includes a sensing device to measure the physiological health data of the user at regular intervals;
   a wristband worn on the wrist of the user, the wristband comprising a processor and a non-transitory computer readable medium storing instructions executable by the processor, wherein the wristband is in communication with the sensing device;
   a computing device in communication with the sensing device in the wearable device and the wristband through a server via a network,
   wherein the server is configured to:
   receive real-time physiological data of the user from the sensing device through the processor;
      collect medical records and health plan data of the user from external sources, including, fitness devices, electronic medical records and payor databases;
      analyze the physiological data of the user, the medical records, and the health plan data through a data processing unit and compare the analysis results with personalized threshold values through an artificial intelligence module;
      wherein the artificial intelligence module comprises:
         a k-nearest-neighbors (KNN) classifier configured to classify real-time physiological data from the sensing device to identify user-health states; and
         a large language model (LLM) incorporating a self-attention mechanism configured to analyze the classified data from the KNN classifier together with the medical records and the health plan data of the user obtained from the external sources to generate personalized health risk assessments, preventive care recommendations, and natural-language explanations describing a current health status of the user and recommended actions for the user, the LLM employing reinforcement-learning techniques to adapt its output generation to historical trends and inputs of the physiological data of the user; and wherein the LLM is further configured to adapt to predefined health risk threshold values for the physiological data of the user and emphasize clinically significant numerical values for the physiological data of the user to improve accuracy of the generated personalized health risk assessments and improve the preventive care recommendations.

2. The apparatus of claim 1, wherein the server is configured to send one or more alerts to the user in response to detection of abnormal physiological data, where the abnormal physiological data are detected when the physiological data of the user exceed the predefined health risk threshold values for the physiological data of the user, where the LLM provides the natural-language explanations and recommended actions through the computing device.

3. The apparatus of claim 1, wherein the physiological data of the user include at least one of a body temperature, a heart rate, a respiratory rate, blood oxygen levels, mental state resilience metrics, hydration levels, glucose levels and a blood pressure, where the physiological data of the user are analyzed by the LLM to enhance accuracy of the LLM-generated personalized health risk assessment through continuous learning and LLM-based context-aware predictions.

4. The apparatus of claim 1, wherein the server is further configured to generate at least one progress report based on the physiological health data of the user and share the generated progress report with the user and the care team through the computing device, the LLM continuously updating the progress report based on newly received data from the sensing device.

5. The apparatus of claim 1, wherein the apparatus is configured to wirelessly communicate with one or more external fitness devices and computing devices through the network for real-time synchronization.

6. The apparatus of claim 1, wherein the server is further configured to:

execute control instructions, in response to the analysis, to modify operation of the computing device, or to initiate at least one alert that includes one or more of a hydration reminder and wellness reminder;

predict risk of critical illness and determine preventive-care options comprising at least one of dietary changes, exercise regimens, hydration reminders, relaxation guidance, and medication schedules; and display, on the computing device, the physiological data of the user, the LLM-generated personalized health risk assessments, and the corresponding preventive care recommendations.

7. The apparatus of claim 6, wherein the server is further configured to generate charts and graphs with timelines to visualize the physiological health data of the user and display them through the computing device, wherein these visualizations are updated in real-time based on the LLM's ongoing analysis.

8. The apparatus of claim 6, wherein the preventive care recommendations determined by the LLM comprise at least one of dietary changes, exercise regimens, and medication reminders with personalized recommendations generated based on real-time data analysis by the LLM, considering both historical health data of the user and the user's current physiological status.

9. A method of monitoring, tracking, and storing physiological data of a user through an apparatus, comprising:

(a) monitoring, by a sensing device of the apparatus, physiological data of the user at regular intervals, wherein the sensing device forms a part of a wearable device worn on at least one finger of the user's hand;

(b) transferring, by a processor disposed within a wristband and which is in communication with the sensing device, data related to the physiological data of the user to a server;

(c) collecting, by the server through a data processing unit, physiological data of the user, medical records and health plan data of the user from external sources, including one or more of personal fitness devices, electronic medical records systems, and payor databases; and (d) analyzing, by the server through a data-processing unit, the physiological-parameter data, the medical records, and the health-plan data, and comparing analysis results with personalized threshold values through an artificial intelligence module comprising a large language model (LLM) and a k-nearest neighbors (KNN) classifier;

wherein the KNN classifier is configured to classify real-time physiological data of the user from the sensing device to identify user-health states; and wherein the LLM incorporates a self-attention mechanism and employs reinforcement-learning techniques to adapt output generation to user patterns and the LLM is configured to:

analyze the classified data together with medical records and health plan data obtained from external sources, adaptively update personalized thresholds, and generate personalized health risk assessments, preventive care recommendations, and natural-language explanations describing a current health status of the user and recommended actions for the user.

10. The method of claim 9, wherein the physiological data of the user include a body temperature, a heart rate, a respiratory rate, blood oxygen levels, mental state resilience, hydration levels, glucose levels, and a blood pressure that are interpreted by the LLM to enhance accuracy of assessing a health condition of the user.

11. The method of claim 9, wherein the apparatus wirelessly communicates with external fitness devices and computing devices through the network for real-time synchronization and LLM-based continuous health analysis.

12. The method of claim 9, further comprising:

executing, by the server, control instructions, in response to the analysis, to modify operation of a computing device, or to initiate at least one alert that includes one or more of a hydration reminder and wellness reminder;

predicting, by the server, risk of critical illness and determining preventive-care options comprising at least one of dietary changes, exercise regimens, hydration reminders, relaxation guidance, and medication schedules; and displaying, on the computing device, the physiological data of the user, the LLM-generated personalized health risk assessments, and the corresponding preventive care recommendations.

13. The method of claim 12, wherein the server sends one or more alerts to the user and care team in response to detection of abnormal threshold values of the physiological data of the user, the LLM providing contextual explanations and recommended actions for the user through the computing device.

14. The method of claim 12, wherein the server generates at least one progress report based on the physiological health data of the user and share the progress report with the user and the care team through the computing device, wherein the LLM continuously updates the progress report based on newly received data from the sensing device.

15. The method of claim 12, wherein the server generates charts and graphs with timelines to visualize the physiological data of the user and display them through the computing device, the visualizations being dynamically updated in real-time as the LLM processes newly received data.

16. The method of claim 12, wherein the preventive care recommendations comprise at least one of dietary changes, exercise regimens, hydration reminders, relaxation guidance, and medication schedules with personalized recommendations generated based on real-time data analysis by the LLM, considering both historical health data of the user and a current physiological status of the user.

\* \* \* \* \*